United States Patent
Polley et al.

(10) Patent No.: US 10,187,940 B2
(45) Date of Patent: Jan. 22, 2019

(54) TRANSMITTER ARCHITECTURE FOR PHOTOPLETHYSMOGRAPHY SYSTEMS

(71) Applicant: Texas Instruments Incorporated, Dallas, TX (US)

(72) Inventors: Arup Polley, Richardson, TX (US); Ajit Sharma, Dallas, TX (US); Srinath Ramaswamy, Murphy, TX (US); Sriram Narayanan, Richardson, TX (US)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 77 days.

(21) Appl. No.: 15/131,831

(22) Filed: Apr. 18, 2016

(65) Prior Publication Data

US 2017/0099711 A1    Apr. 6, 2017

Related U.S. Application Data

(60) Provisional application No. 62/236,589, filed on Oct. 2, 2015.

(51) Int. Cl.
   *H05B 33/08*     (2006.01)
   *A61B 5/024*     (2006.01)
   *A61B 5/1455*    (2006.01)
   *A61B 5/00*      (2006.01)

(52) U.S. Cl.
   CPC ..... *H05B 33/0818* (2013.01); *A61B 5/02427* (2013.01); *A61B 5/14551* (2013.01); *A61B 5/7225* (2013.01)

(58) Field of Classification Search
   None
   See application file for complete search history.

(56) References Cited

U.S. PATENT DOCUMENTS 5,179,565 A * 1/1993 Tsuchiya ................ G01R 15/22
                                                     372/26

OTHER PUBLICATIONS

Saadeh et al., "A >89% Efficient LED Driver with 0.5V Supply Voltage for Applications Requiring Low Average Current", 2013 IEEE Asian Solid-State Circuits Conference (IEEE, 2013), pp. 273-276.

(Continued)

*Primary Examiner* — Douglas W Owens
*Assistant Examiner* — Jianzi Chen
(74) *Attorney, Agent, or Firm* — Michael A. Davis, Jr.; Charles A. Brill; Frank D. Cimino (57) ABSTRACT

An LED (light-emitting diode) driver for a photoplethysmography system, including a switched-mode operational amplifier for driving a driver transistor with a source-drain path in series with the LED. In a first clock phase in which the LED is disconnected from the driver transistor, the amplifier is coupled in unity gain mode, and a sampling capacitor stores a voltage corresponding to the offset and flicker noise of the amplifier; the gate of the driver transistor is precharged to a reference voltage in this first clock phase. In a second clock phase, the sampled voltage at the capacitor is subtracted from the reference voltage applied to the amplifier input, so that the LED drive is adjusted according to the sampled noise. A signal from the transmitter channel is forwarded to a noise/ripple remover in the receiving channel, to remove transmitter noise from the received signal.

12 Claims, 4 Drawing Sheets

(56) References Cited

OTHER PUBLICATIONS

"AFE4400 Integrated Analog Front-End for Heart Rate Monitors and Low-Cost Pulse Oximeters", Data Sheet SBAS601H (Texas Instruments Incorporated, Jul. 2014).
Kugelstadt, "Auto-zero amplifiers ease the design of high-precision circuits", Analog Applications Journal (Texas Instruments Incorporated, 2005), p. 19-27.

* cited by examiner

TRANSMITTER ARCHITECTURE FOR PHOTOPLETHYSMOGRAPHY SYSTEMS

CROSS-REFERENCE TO RELATED APPLICATIONS

This application claims priority, under 35 U.S.C. § 119(e), of Provisional Application No. 62/236,589, filed Oct. 2, 2015, incorporated herein by this reference.

STATEMENT REGARDING FEDERALLY SPONSORED RESEARCH OR DEVELOPMENT

Not applicable.

BACKGROUND OF THE INVENTION

This invention is in the field of circuitry for driving light-emitting diodes (LEDs). Embodiments are more specifically directed to LED driver circuitry in transmitters of photoplethysmography (PPG) systems.

Photoplethysmography (PPG) is a modern technology that has proven useful for the measurement of cardiovascular function in humans. According to this technology, fixed wavelength light from a light-emitting diode (LED) is emitted into the skin of a human subject, and is sensed by a photodiode (PD) after transmission through the skin and underlying tissue. The characteristics of the sensed light allows measurement of medical parameters such as oxygenation, pulse rate, respiratory function, and the like.

Conventional PPG sensors include the well-known pulse oximeter, for example of the type that clip-on onto the finger of the patient. Pulse oximeters typically measure the oxygen saturation of circulating blood from a comparison of the absorption of light in the dermis and subcutaneous tissue at two different wavelengths. So-called "wearable" devices such as heart rate sensors also utilize this technology, but need only measure light absorption at a single wavelength.

Figure 1:
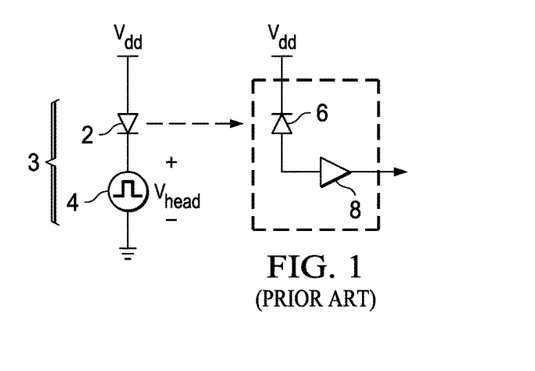
FIG. 1 is an electrical diagram, in schematic form, of a generic architecture for a conventional photoplethysmography (PPG) system.

FIG. 1 generically illustrates the architecture of a conventional PPG system. Transmitter 3 in this system includes LED 2, which has its anode biased by the $V_{dd}$ power supply voltage and its cathode coupled to ground via LED driver 4. As mentioned above, PPG pulse oximeters will included multiple LEDs 2 (e.g., red and infrared), operated in time-multiplexed fashion. When forward-biased by LED driver 4, LED 2 emits light into the patient, for example the index finger of the patient. Receiver 7 includes photodiode 6, which has its cathode biased at the $V_{dd}$ power supply voltage and its anode connected to the input of amplifier 8, and which is normally reverse-biased so that photons impinging photodiode 6 will produce a current detectable by amplifier 8. In this manner, photodiode 6 senses the extent to which the light emitted by LED 2 is transmitted through the subject. The output of amplifier 8 is forwarded to the desired processing and analysis circuitry of the PPG system to determine the desired medical measurement, such as the oxygenation of the patient's blood.

Figure 2:
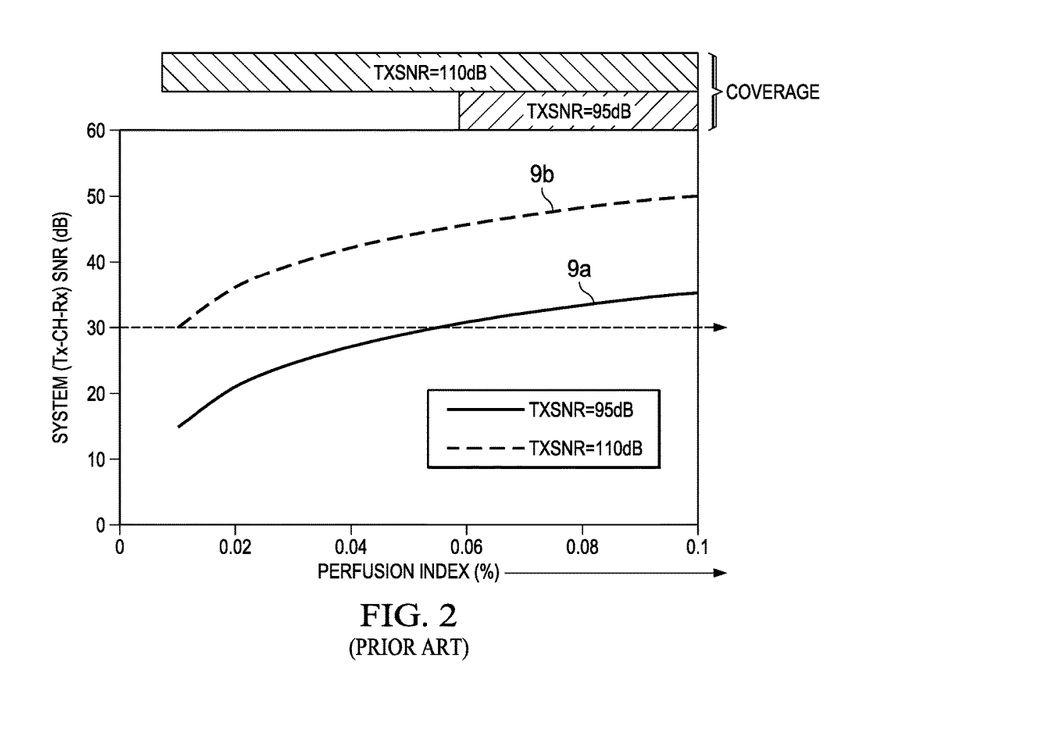
FIG. 2 illustrates plots of signal-to-noise ratio (SNR) of conventional PPG systems having different transmitter SNRs versus perfusion index.

The ability of any PPG system to accurately and precisely measure the parameter of interest is based on the signal-to-noise ratio (SNR) of the overall system, considering both its transmitter and receiver. For example, it has been observed that an SNR of at least about 30 dB, for the PPG system as a whole including the transmission channel through patient tissue, is necessary in order to measure pulse rate to an accuracy of 1 beat per minute (bpm). A complicating factor in practice is that the system SNR depends on the perfusion index of the patient, as illustrated in FIG. 2. Perfusion index is the ratio of the AC signal due to pulsatile blood flow to the DC background level of the light signal passing through the patient's peripheral tissue, and depends largely on the health and physical condition of the patient. As such, for the PPG system of FIG. 1, the perfusion index is reflected in the amplitude of the AC pulses of the received light (e.g., as output by amplifier 8) relative to its DC level. As shown in FIG. 2, the system SNR increases at higher perfusion index values.

Conversely, if the SNR of the PPG system can be increased, the system can measure the pulse rate and blood oxygenation in a wider range of patients, particularly those of poorer health and thus lower perfusion indices. FIG. 2 shows two SNR vs. perfusion index plots 9a, 9b. Plot 9a illustrates the relationship of system (transmit—channel—receive) SNR to perfusion index for the case in which the transmitter SNR is 95 dB; as known in the art, to attain the required system SNR, the SNRs for the transmitter and receiver must both be higher than that required system SNR. At that transmit SNR, the PPG system is able to measure pulse rate to an accuracy of one bpm only for patients exhibiting a perfusion index of at least about 0.06. In contrast, plot 9b illustrates that if the transmitter is able to operate at an SNR of 110 dB, pulse rate measurements at an error of 1 bpm can be made for patients with perfusion index values as low as about 0.01. Accordingly, noise in the transmitter of the PPG system is a critical factor in covering a wide range of patients.

So-called "wearable" electronic devices, such as fitness monitoring devices, have recently become popular. In addition to fitness monitoring devices, wearable medical monitoring devices are being contemplated for use in healthcare, for example to monitor the recovery or progress of a patient suffering from a medical condition. As such, the use of PPG to obtain oxygenation, pulse rate, and other measurements by way of a wearable device, particularly such a device that can be worn all day, is desirable. In this context, battery life becomes of critical performance.

In this regard, an important electrical parameter of a transmitter in a battery-powered system, such as a wearable device, is the "headroom" of the LED driver. As well-known by those in the art, it is desirable that battery-powered systems operate at low power supply voltages to reduce power consumption and to reduce the cost of the battery itself. In transmitter 3 of FIG. 1, the voltage drop across LED 2 in its operating state is defined by its material. The headroom, shown as $V_{head}$ in FIG. 1, is the voltage required by LED driver 4 beyond the LED voltage drop. Conversely, the minimum $V_{dd}$ power supply voltage is the sum of the voltage drop across LED 2 and the headroom $V_{head}$ of LED driver 4. For battery powered systems, therefore, it is desirable that the headroom $V_{head}$ required by LED driver 4 be minimized, especially considering that the output voltage from conventional batteries tends to sag over time.

As mentioned above, it is desirable to minimize power consumption in PPG systems, particularly those in battery-powered wearable devices intended for "all-day" use. Duty cycling of LED driver 4 in transmitter 3 is a common approach to reducing system power consumption. It is therefore desirable for LED driver 4 to exhibit fast switching, and rapid settling times, so that the "on" pulse width can be reduced as much as possible and thus minimizing power consumption.

Figure 3A:
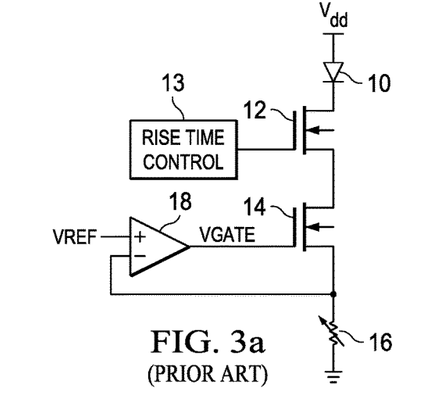
FIGS. 3a through 3c are electrical diagrams, in schematic form, of conventional LED drivers for PPG systems.
Figure 3B:
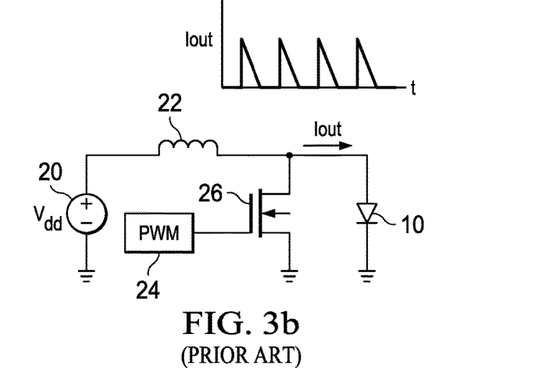
Figure 3C:
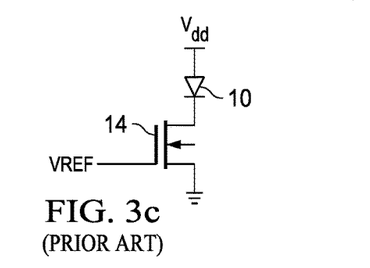

FIGS. 3a through 3c illustrate examples of conventional LED drivers for PPG systems. The circuit of FIG. 3a is an example of a typical LED driver circuit, such as used in a PPG system as described above. In this circuit, LED 10 has its anode at the $V_{dd}$ power supply voltage and its cathode connected to the drain of rise time control n-channel MOS transistor 12. Transistor 12 has its source connected to the drain of n-channel driver transistor 14, which is connected to ground via variable resistor 16. Resistor 16 operates to control the current drawn through LED 10 and transistor 12, at a resistance typically set by a digital-to-analog converter (DAC). The gate of transistor 12 receives a control voltage from rise time controller 13, which is an adjustable circuit block that controls the conduction of transistor 12 to attain the desired rise and fall times in the turn-on and turn-off characteristics of LED 10. Amplifier 18 receives a reference voltage VREF at its non-inverting (positive) input and a feedback voltage from the source of transistor 14 at its inverting (negative) input. Output voltage VGATE from amplifier 18 is applied to the gate of driver transistor 14. According to this arrangement, amplifier 18 operates to drive the gate voltage VGATE at driver transistor 14 so that reference voltage VREF at the source node of transistor 14. Reference voltage VREF is modulated to selectively forward bias LED 10.

The LED driver circuit of FIG. 3a provides certain advantages in a PPG system. Specifically, variable resistor 16 tends to reduce the transmitter noise in this circuit, and the ripple exhibited by this circuit is also quite low. However, it has been observed that this arrangement is vulnerable to significant input flicker noise from amplifier 16, degrading transmitter performance. The settling time of this LED driver is also quite slow, due to the bandwidth of amplifier 18. In addition, the LED driver of FIG. 3a is not conducive to implementation in low voltage, battery-powered, applications because of its large headroom voltage, specifically the sum of the drain-to-source overdrive voltages of transistors 12 and 14 plus the voltage drop across resistor 16.

FIG. 3b illustrates a conventional LED driver with very low headroom requirements as useful for a PPG system. In this circuit, power supply 20 applies the $V_{dd}$ bias to LED 10 through inductor 22. N-channel driver transistor 26 has its source-drain path connected in parallel with LED 10 between inductor 22 and ground. The gate of transistor 26 receives the output of pulse-width modulator (PWM) 24. During the "off" pulses, transistor 26 shunts the inductor current through inductor 22 to ground; during the "on" pulses, the $V_{dd}$ power supply voltage forward biases LED 10, such that the inductor current is conducted through LED 10 to ground. FIG. 3b illustrates the behavior of output current $I_{out}$ through LED 10 over a sequence of pulses from PWM 24, illustrating that the output current $I_{out}$ appears as a sequence of triangle waves. While the headroom required by this LED driver is quite low, it has been observed that transmitter noise is quite high in this arrangement, which reduces the patient coverage as discussed above relative to FIG. 2. In addition, significant ripple is present in the LED driver of FIG. 3b.

In the circuit of FIG. 3c, LED 10 has its anode at the $V_{dd}$ power supply voltage and its cathode connected to the drain of n-channel MOS transistor 14; the source of transistor 14 is at ground. A reference voltage VREF is applied to the gate of transistor 14, and is modulated to turn LED 10 on and off, thus controlling the emission of light. This simple driver of FIG. 3c has a low headroom voltage of only the drain-to-source voltage overdrive of transistor 14, and exhibits no ripple. However, because the driver of FIG. 3c is quite noisy, its use in the transmitter of a PPG system will have limited patient coverage, as discussed above relative to FIG. 2.

By way of further background, auto-zeroing techniques for removing offset voltage and drift of operational amplifiers are known in the art, as described in Kugelstadt, "Auto-zero amplifiers ease the design of high-precision circuits", *Analog Applications Journal*, 2Q 2005 (Texas Instruments Incorporated), pp. 19-28, incorporated herein by reference.

BRIEF SUMMARY OF THE INVENTION

Disclosed embodiments provide an LED driver that reduces transmitter noise, when incorporated into a photoplethysmography (PPG) system.

Disclosed embodiments provide such an LED driver that reduces the transmitter settling time, by reducing LED turn-on time, and is thus capable of operating with lower power consumption than conventional LED driver circuits.

Disclosed embodiments provide such an LED driver that has minimal headroom voltage requirements.

Disclosed embodiments provide such an LED driver that, when implemented in the transmitter of a pulse oximeter or heart rate monitor, increases the patient coverage with respect to perfusion index.

Other objects and advantages of the disclosed embodiments will be apparent to those of ordinary skill in the art having reference to the following specification together with its drawings.

According to certain embodiments, an LED driver circuit, such as useful for use in a photoplethysmography (PPG) system, includes a driver transistor connected in series with a variable current control resistor and the LED itself. A switched-mode amplifier circuit drives the gate of the driver transistor in two non-overlapping clock phases during an "on" pulse. In a first phase, noise and offset of the amplifier is stored as a voltage by a capacitor coupled between an amplifier input and the output of the amplifier. Also in this first phase, a precharge capacitor between the gate of the driver transistor and a ground node is precharged to a reference voltage level. In a second phase, the voltage applied to the amplifier input is compensated by the stored sampled noise voltage and is not reflected at the gate voltage of the driver transistor as it turns on the LED. The voltage swing of the driver gate voltage in this second phase is reduced by the precharge applied in the first phase.

According to another embodiment, a PPG system is constructed to include a transmitter with an LED driver that is co-located with a photodiode receiver. A linear estimate of ripple and noise current in the transmitter is forwarded to a noise and ripple remover circuit in the receiver to recover the signal component of the light signal received by the photodiode.

BRIEF DESCRIPTION OF THE SEVERAL VIEWS OF THE DRAWING

FIGS. 6b and 6c are electrical diagrams, in schematic form, illustrating the operation of the LED driver of FIG. 5 in respective clock phases as shown in FIG. 6a.

DETAILED DESCRIPTION OF THE INVENTION

The one or more embodiments described in this specification are implemented into a photoplethysmography (PPG) system such as used in pulse oximetry, as it is contemplated that such implementation is particularly advantageous in that context. However, it is also contemplated that concepts of this invention may be beneficially applied to other applications involving the transmission and receipt of optical signals. Accordingly, it is to be understood that the following description is provided by way of example only, and is not intended to limit the true scope of this invention as claimed.

Figure 4:
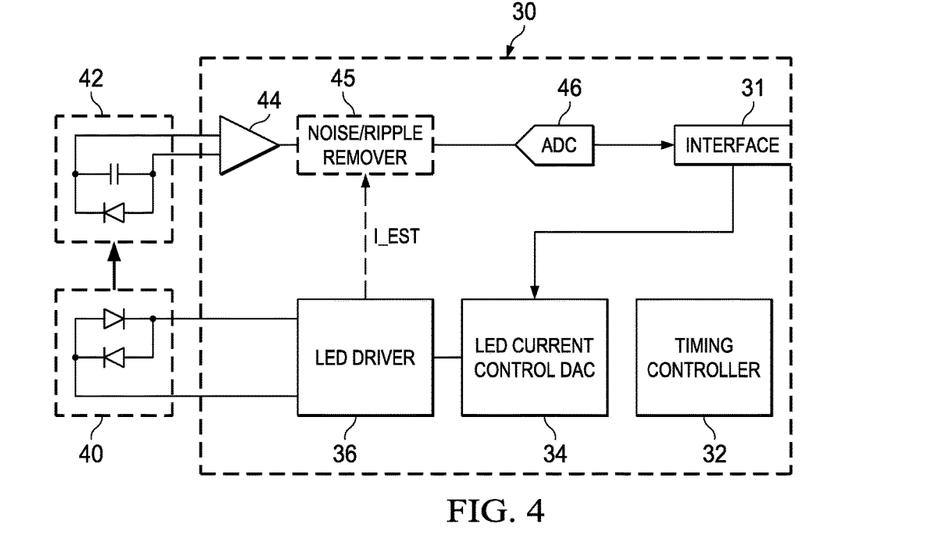
FIG. 4 is an electrical diagram, in block form, of a PPG system in which embodiments may be implemented.

Referring now to FIG. 4, the construction and operation of a PPG system, for example serving as a pulse oximeter and heart rate monitor, and in which these embodiments may be implemented will be described. As shown in FIG. 4, this system includes analog front end (AFE) 30, in which both a transmitter channel and a receiver channel are implemented. The transmitter channel of AFE 30 operates to drive one or more light-emitting diodes (LEDs) 40 connected externally to AFE 30. For the example of a pulse oximeter, LEDs 40 are constituted as a pair of LEDs of different colors, for example red and infrared, or red and green. An example of a conventional AFE for pulse oximeters and heart rate monitor is the AFE 4400 integrated AFE available from Texas Instruments Incorporated, described in "AFE4400 Integrated Analog Front-End for Heart Rate Monitors and Low-Cost Pulse Oximeters", Data Sheet SBAS601H (Texas Instruments Incorporated, 2014), incorporated herein by this reference.

The receiver channel of AFE 42 operates to detect and process electrical signals from photodiode receptor 42, which is also connected externally to AFE 30. In this example, receiver channel of AFE 30 according to this embodiment includes amplifier 44, which is connected to external photodiode receptor 42 and which operates to amplify the signal provided by receptor 42. The output of amplifier 44 is coupled to the input of analog-to-digital converter (ADC) 46 (via optional noise remover 45, which will be further described below according to an embodiment), which processes and digitizes the amplified photodiode signal in the conventional manner. Interface 31 communicates that received signal to the appropriate processor circuitry (not shown) for analysis and display of the various attributes indicated by the received signal.

The transmitter channel of AFE 30 in this example includes LED current control digital-to-analog converter (DAC) 34, which receives signals indicative of the desired operating mode and functionality of LEDs 40, from external processor or other circuitry via interface 31. In response, LED current control DAC 34 forwards control signals to LED driver 36, which in turn applies the desired excitation to LEDs 40, specifically by controlling the forward bias current of LEDs 40 and correspondingly the intensity of the emitted light. LED driver 36 may also optionally provide signal to an optional noise/ripple remover 45 in the receiver channel, as will be further described below in connection with an additional embodiment.

AFE 30 also includes timing controller 32, which at least in part controls the operation of transmitter and receiver channels. Other power, diagnostic, and control functions may also be provided within AFE 30, as conventional in the art.

Figure 5:
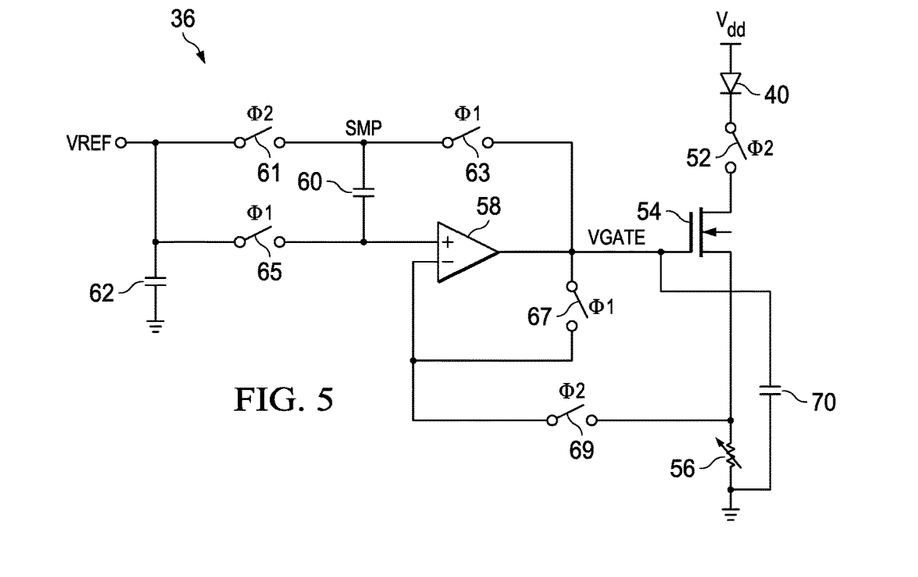
FIG. 5 is an electrical diagram, in schematic form, of a transmitter in a PPG system including an LED driver constructed according to an embodiment.

Referring now to FIG. 5, the construction of LED driver 36 according to an embodiment will now be described. In this embodiment, LED driver 36 controls the light emitted by LED 40 by applying a voltage VGATE at the gate of n-channel metal-oxide-semiconductor (MOS) driver transistor 54. While a single LED 40 is illustrated in the schematic diagram of this FIG. 5, it is contemplated that this LED 40 may be one of a pair of LEDs such as used in a pulse oximeter; in that case, the schematic of FIG. 5 illustrates the manner in which that one of the pair of LEDs is driven in operation. It is contemplated that those skilled in the art having reference to this specification will be readily arrange LED driver 36 to drive the other LED in the pair, for example according to one of the arrangements described in the above-incorporated AFE4400 data sheet.

In the arrangement of FIG. 5, the anode of LED 40 is biased at the $V_{dd}$ power supply voltage, and its cathode is coupled by switch 52 to the drain of driver transistor 54. The source of transistor 54 is coupled to ground via variable current control resistor 56. The resistance of this current control resistor 56 is controlled by LED current control DAC 34, which as mentioned above operates to control the amplitude of the light emitted by LED 40. In this embodiment as shown in FIG. 5, capacitor 70 is present between the gate of driver transistor 54 and the ground node. It is contemplated that this capacitor 70 will typically be constituted by the parasitic gate-to-body node capacitance of driver transistor 54, but if desired or necessary for the functionality described below, may be supplemented by an additional capacitor.

LED driver 36 receives reference voltage VREF, as may be applied from externally to AFE 30 or generated within AFE 30 by a conventional bandgap circuit or other voltage reference circuit. As will be evident from the following description, reference voltage VREF determines the voltage VGATE applied to the gate of driver transistor in its "on" state, that is when LED 40 is to be emitting light. The input receiving reference voltage VREF is connected through switch 61 to one plate of capacitor 60, at sample node SMP, and through switch 65 to an opposite plate of capacitor 60 and the non-inverting (positive) input of amplifier 58. Capacitor 62 is connected between the VREF input and ground, to absorb noise. The output of amplifier 58 is connected to sample node SMP through switch 63, to the inverting (negative) input of amplifier 58 through switch 67, and to the gate of n-channel driver transistor 54. Switch 69 couples the source of driver transistor 54 to the inverting input of amplifier 58.

Each of switches 52, 61, 63, 65, 67, 69 of LED driver 36 is controlled by one of two clock phases Φ1 and Φ2 generated by timing controller 32 (FIG. 4). Each of switches 52, 61, 63, 65, 67, 69 may be realized as a MOS pass gate, for example realized as a single MOS transistor receiving the corresponding gate voltage corresponding to its clock phase, or as paired p-channel and n-channel MOS transistors with their source-drain paths connected in parallel and receiving complementary gate voltages.

Figure 6A:
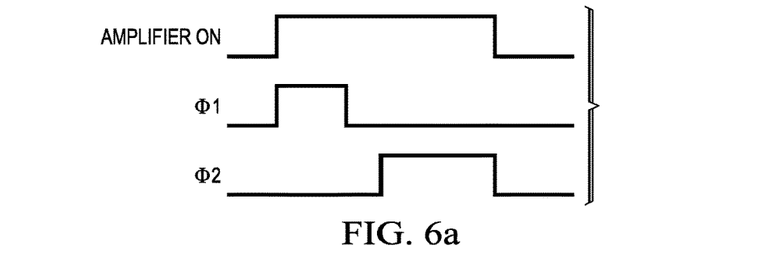
FIG. 6a is a timing diagram illustrating clock phases in the operation of the LED driver of FIG. 5 according to an embodiment.

Specifically, switches 63, 65, and 67 are controlled by clock phase Φ1, specifically to be closed when clock phase Φ1 is at an active high level, while switches 52, 61, and 69 are similarly controlled by clock phase Φ2. FIG. 6a illustrates the relationship of clock phases Φ1 and Φ2 as generated by timing controller 32 in this embodiment. As shown in FIG. 6a, these clock phases Φ1 and Φ2 are non-overlapping clock pulses that are driven to an active high level during the duration of an enable signal applied to amplifier 58, which corresponds to the duration of light emission from LED 40.

According to this embodiment, LED driver 36 operates in clock phase Φ1 to precharge the gate voltage VGATE of driver transistor 54 to a voltage about at the level of reference voltage VREF, and to sample the offset and "flicker" noise of amplifier 58; LED 40 is not driven to emit light during clock phase Φ1. LED driver 36 operates in clock phase Φ2 to drive amplifier 58 with an input voltage corresponding to reference voltage VREF, compensated for the offset and noise sampled during clock phase Φ1. Driver transistor 54 is turned on by the voltage VGATE at the output of amplifier 58 in response to this compensated voltage at its non-inverting input, and LED 40 emits light accordingly. As will be evident from this description, this noise compensation at the voltage applied to amplifier 58 minimizes the undesired noise and ripple that is typically present in conventional LED driver circuits with low headroom requirements.

Figure 6B:
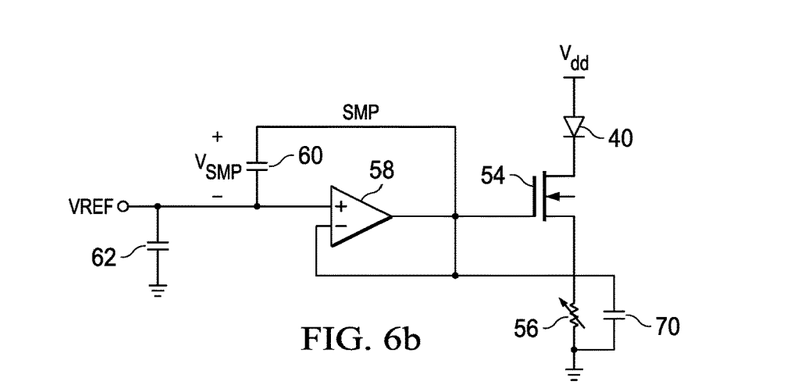
Figure 6C:
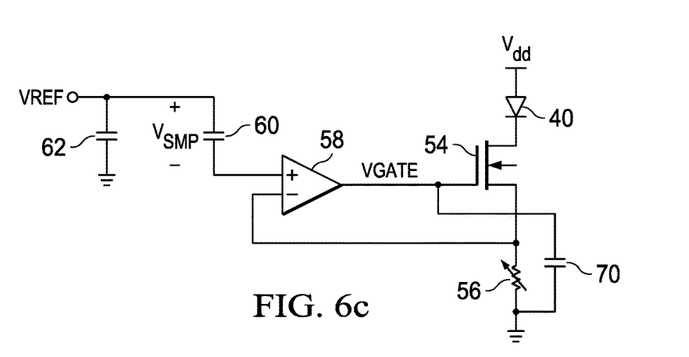

FIGS. 6b and 6c illustrate the operation of LED driver 36 in clock phases Φ1 and Φ2, respectively. In FIG. 6b, switches 63, 65, and 67 are closed during clock phase Φ1, and switches 52, 61, and 69 are open. As such, the VREF input is connected to the non-inverting input of amplifier 58 via switch 65, and sample node SMP at the opposing plate of capacitor 60 is connected to the output of amplifier 58 via switch 63. The output of amplifier 58 is also directly connected to the inverting input of amplifier 58 via switch 67. The cathode of LED 40 is disconnected from the drain of driver transistor 54, and as such LED 40 emits no light during clock phase Φ1.

With LED driver 36 in the state shown in FIG. 6b during clock phase Φ1, amplifier 58 is in unity gain mode, since its output is connected directly to its inverting input through closed switch 67. This unity gain arrangement causes amplifier 58 to drive its output to reference voltage VREF at its non-inverting input. Sampling capacitor 60, connected between the non-inverting input and the output of amplifier 58, will charge to a voltage $V_{SMP}$ corresponding to the offset plus "flicker" or 1/f noise of amplifier 58. Meanwhile, capacitor 70 charges to the voltage at the output of amplifier 58, which as noted above, is at reference voltage VREF, which in turn precharges the gate of driver transistor 54 to about the level of VREF, in anticipation of clock phase Φ2.

In clock phase Φ2, LED driver 36 is in the state shown in FIG. 6c, with switches 63, 65, and 67 open and switches 52, 61, and 69 closed. The cathode of LED 40 is connected to the drain of driver transistor 54 through the closed switch 52, such that the bias condition of LED 40, and thus whether it emits light, is controlled by the state of driver transistor 54. The inverting input of amplifier 58 is now connected to the source of driver transistor 54, at the node between transistor 54 and variable resistor 56, since switch 69 is closed and switch 67 is open in this clock phase Φ2. And the VREF input is coupled to the non-inverting input of amplifier 58 via capacitor 60, by the action of switch 61 being closed and switch 65 being open.

According to this embodiment, therefore, the voltage applied to the non-inverting input of amplifier 58 is reference voltage VREF minus the voltage $V_{SMP}$ stored across capacitor 60 during clock phase Φ1. Since this voltage $V_{SMP}$ across capacitor 60 corresponds to the offset and noise of amplifier 58, as sampled in clock phase Φ1, the input voltage applied to the non-inverting input of amplifier 58 is compensated for this offset and noise. The drive applied by amplifier 58 as gate voltage VGATE to driver transistor 54 is thus compensated for offset and noise, which in turn compensates the intensity of the light emitted by LED 40 for the offset and noise at amplifier 58. By reducing the noise in the emitted light in this fashion, the transmitter SNR is improved according to this embodiment.

Because the "flicker" noise of typical amplifiers, such as an op amp or the like used to realize amplifier 58, is primarily low frequency noise (i.e., flicker noise often being referred to as 1/f noise) and because offset is essentially at DC, little variation is expected between the offset plus noise when sampled during clock phase Φ1, and when compensated during clock phase Φ2. It is therefore contemplated that the accuracy of this compensation will generally be quite good. The noise and offset performance of LED driver 36 according to this embodiment is therefore contemplated to be significantly improved over conventional LED driver circuits, particularly those with low headroom as described above.

In addition, the precharging of gate voltage VGATE to the reference voltage VREF during clock phase Φ1, according to this embodiment, is contemplated to significantly reduce the voltage swing required at the gate of driver transistor 54 when turning on LED 40 in clock phase Φ2. It is expected that the voltage at the source of driver transistor 54 will generally be near reference voltage VREF, on one side or the other, depending on the desired current as controlled via variable resistor 56. Accordingly, the reduced voltage swing of gate voltage VGATE provided by this precharging is expected to greatly reduce the settling time of LED driver 36, enabling operation of the PPG system at shorter "on" pulse widths, and thus saving battery power.

In addition, the headroom requirement of LED driver 36 according to this embodiment is reduced from conventional arrangements such as that described above relative to FIG. 3a. Referring to FIG. 5, the headroom required in LED driver 36 is the sum of the voltage drop across variable resistor 56 plus the drain-to-source overdrive of driver transistor 54. Conversely, the conventional LED driver of FIG. 3a requires headroom that includes the overdrive of two MOS transistors. Accordingly, this embodiment provides an LED driver having relatively low headroom requirements as compared with conventional drivers, while also achieving good noise performance and also fast settling times.

According to another embodiment, a PPG system is provided that is constructed and operated to provide additional compensation for transmitter noise and ripple. It is contemplated that this embodiment will be especially beneficial when implemented in PPG systems in which transmitter 80 and receiver 85 are "co-located", for example integrated into the same integrated circuit as one another, or at least in very close proximity with one another.

FIG. 4 illustrates this embodiment in a general sense by way of optional noise/ripple remover function 45 in the receiver channel of AFE 30, between amplifier 44 and ADC 46. As shown in FIG. 4, noise/ripple remover 45 receives time-domain signal I_EST from LED driver 36. This signal I_EST corresponds to the current conducted by LED 40 in its on state, including ripple and other transmitter noise in that current. Because the intensity of the light emitted by an LED is proportional to the forward-bias current, it is contemplated, according to this embodiment, that variations due to noise and ripple in the current applied by LED driver 36 will reflect transmitter noise in the light emitted by LED 40.

Figure 7A:
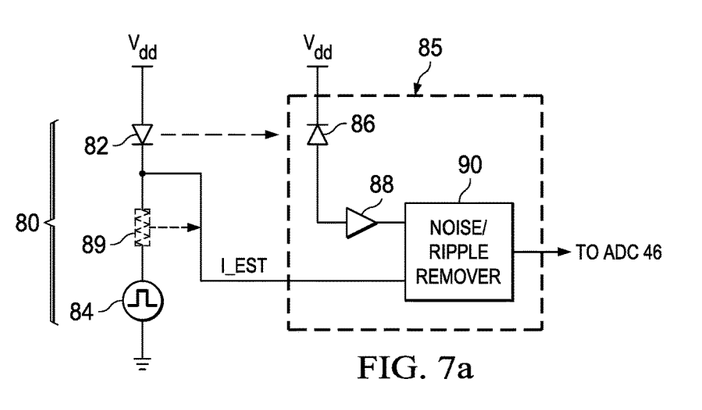
FIG. 7a is an electrical diagram, in block and schematic form, of a PPG system constructed according to another embodiment.
Figure 7B:
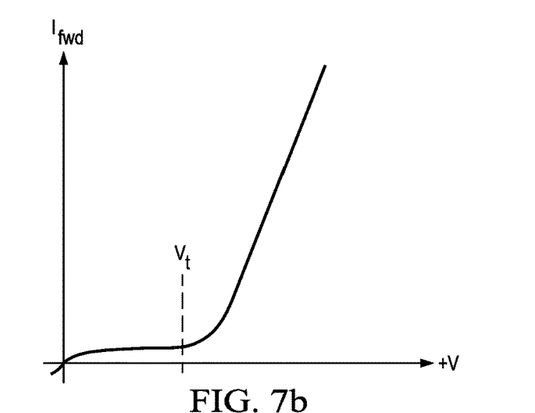
FIG. 7b is a plot of forward current versus voltage for the LED driven by an LED driver according to disclosed embodiments.

FIGS. 7a and 7b illustrate an example of a PPG system including transmitter channel 80 and receiver channel 85 constructed according to this embodiment. Transmitter channel 80 in this PPG system includes LED 82 and LED driver 84 connected in series between the $V_{dd}$ power supply voltage and ground. LED driver 84 may be constructed in the manner described above relative to FIGS. 5 and 6a through 6c; alternatively, LED driver 84 may be constructed according to one of any other conventional LED driver arrangements. In this embodiment, signal I_EST corresponding to the current conducted by LED 82 is communicated from transmitter 80 to receiver 85, in the form of a sensed voltage at a node in the LED current path from which the current can be deduced, or as a signal corresponding to a direct measure of the conducted current. For example, if LED driver 84 is constructed as described above relative to FIG. 5, this sensed voltage may be taken across resistor 56, or across a small linear current sensing resistor (not shown) in the LED current path.

Receiver channel 85 includes photodiode 86 with its cathode at the $V_{dd}$ power supply and its anode connected to an input of amplifier 88, as conventional in the art. According to this embodiment, however, and as also illustrated in FIG. 4 discussed above, receiver channel 85 includes noise/ripple remover function 90 (which corresponds to noise/ripple remover function 45 of FIG. 4). Noise/ripple remover 90 may be constructed by way of the appropriate analog circuits for carrying out the functions described in this specification. In the embodiment of FIG. 4, noise/ripple remover 90 has one input coupled to the output of amplifier 88 to receive the amplified received signal from photodiode 86, and another input receiving the voltage or current signal from transmitter channel 80. As will be described in further detail below, noise/ripple remover 90 removes the estimated transmitter noise in the LED current, and thus in the emitted light, from the amplified signal received from photodiode 86. The output of noise/ripple remover 90 is then forwarded along receiver channel 85 for further processing and communication. Alternatively, noise/ripple remover 45 may be realized in the digital domain (i.e., following ADC 46) as a digital circuit or programmable logic, arranged or programmed to carry out these functions and operations in the digital domain. Further in the alternative, some of the functions and operations of noise/ripple remover 90 may be performed in the analog domain and others in the digital domain following digitization by ADC 46. In any event, it is contemplated that those skilled in the art having reference to this specification will be readily able to implement noise/ripple remover 90 as appropriate to carry out these functions in particular applications, in either the analog or digital domains or in a combination of the two, without undue experimentation.

The operation of noise/ripple remover 90 according to this embodiment will now be described in connection with the manner in which the noise and ripple removal function is performed. One may consider the current $I_{TX}$ conducted by LED 82 as the sum of a signal component $I_{TX0}$ and a noise component $I_{Tx,n}$:

$$I_{TX}=I_{TX0}+I_{TX,n}$$

FIG. 7b is a current-voltage characteristic of a typical LED that may be used as LED 82 in transmitter 80. As shown in this Figure, at applied voltages above some threshold voltage $V_t$, forward current $I_{fwd}$ conducted by the LED is linear with the applied voltage V, to at least a reasonable approximation. Accordingly, it is contemplated that a voltage $V_d$ taken at the cathode of LED 82 in transmitter 80 of FIG. 7a, and communicated to noise/ripple remover 90 as signal I_EST, will similarly be linear with the voltage drop across LED 82, at a slope corresponding to a small-signal ("AC") resistance $R_d$. Accordingly, the voltage $V_d$ can be considered as the sum of a nominal signal voltage component $V_{d0}$ and a noise component:

$$V_d=V_{d0}+R_d I_{TX,n}$$

According to this embodiment, noise/ripple remover function 90 determines nominal signal voltage component $V_{d0}$ by time-averaging the voltage $V_d$ communicated by transmitter channel 80 as signal I_EST. The AC resistance $R_d$ may be determined by characterization or the specifications of LED 82, and programmed or otherwise set at noise/ripple remover function 90 for use in this determination.

The light emitted by LED 82 will be proportional to the current $I_{TX}$ conducted by LED 82, including both the signal and noise components noted above. At receiver channel 85, the voltage $V_{RX}$ at the output of amplifier 88 corresponding to the signal from photodiode 86 can thus be expressed as:

$$V_{RX}=\tilde{G}I_{TX}$$

where $\tilde{G}$ is the transfer function of the medium through which the emitted light passes between LED 82 and photodiode 86 (e.g., the patient's finger in a pulse oximeter application). Breaking down the LED current $I_{TX}$ into its signal and noise components:

$$V_{RX}=\tilde{G}I_{TX0}+\tilde{G}I_{TX,n}$$

which can also be expressed in the voltage domain as the sum of signal and noise components:

$$V_{RX}=V_{RX0}+V_{RX,n}$$

Signal component $V_{RX0}$ is the desired quantity to be processed:

$$V_{RX0} = V_{RX} - V_{RX,n} = V_{RX}\left(1 - \frac{V_{RX,n}}{V_{RX}}\right)$$

The ratio of noise $V_{RX,n}$ to received voltage $V_{RX}$ can be expressed as:

$$\frac{V_{RX,n}}{V_{RX}} = \frac{\tilde{G}I_{TX,n}}{\tilde{G}I_{TX}} = \frac{I_{TX,n}}{I_{TX}}$$

Since the transmitted current noise component $I_{TX,n}$ is:

$$I_{TX,n} = \frac{V_d - V_{d0}}{R_d}$$

the signal component $V_{RX0}$ can be determined as:

$$V_{RX0} = V_{RX}\left(1 - \frac{V_d - V_{d0}}{R_d I_{TX}}\right)$$

Because the received signal $V_{RX}$ from photodiode 86, the signal I_EST from transmitter 80 in the form of voltage $V_d$, a time-average of that voltage $V_d$ as an estimate of nominal voltage $V_{d0}$, the AC resistance $R_d$, and the current $I_{TX}$ as set by LED current control DAC 32 are all available to noise/ripple remover function 90, this equation can be solved by function 90 to determine the voltage signal component $V_{RX0}$. In one implementation example, the subtraction of $V_d-V_{d0}$ may be performed in the analog domain by fixed amplification, followed by digitization (ADC 46) of the difference and completion of the calculation of $V_{RX0}$ in the digital domain. Signal component $V_{RX0}$, from which the effects of noise and ripple are removed according to the foregoing calculations, is then forwarded along receiver channel 85 for processing as desired for the particular application of the PPG system.

Alternatively, as shown in FIG. 7a and as mentioned above, a small resistor 89 may be inserted in series with LED 82 and LED driver 84 to provide a direct measure of current conducted by LED 82 to noise/ripple remover function 90 at receiver 85. In this approach, signal I_EST will correspond to a measured voltage across resistor 89. Further in the alternative, a non-contact current sensor (not shown) may be deployed at transmitter 80 to sense the current conducted during the "on" time of LED 82 and communicate signal I_EST corresponding to that measured current to noise/ripple remover 90 in receiver 85 as shown. According to these alternative current measurements, the estimate of the AC resistance $R_d$ of LED 82 is not necessary, allowing the determination of the signal component of the photodiode signal $V_{RX0}$ in a more direct fashion, without the potential inaccuracy from estimating this resistance.

It is therefore contemplated that this embodiment can further reduce the effect of transmitter noise in the eventual output signal from the receiver channel of a PPG system. This noise reduction is reflected in an improvement of the overall SNR of the PPG system itself. As discussed above relative to FIG. 2, improvement of the system SNR by improving the effective SNR of the transmitter channel (in this embodiment, by compensating for transmitter noise), expands the coverage of the system to patients with lower perfusion index values, and thus expanding the potential applications of PPG in patient monitoring and other applications.

While one or more embodiments have been described in this specification, it is of course contemplated that modifications of, and alternatives to, these embodiments, such modifications and alternatives capable of obtaining one or more the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A driver circuit for a light-emitting diode (LED), the driver circuit comprising:
   a driver transistor having a source, a drain and a gate, wherein a source-drain path of the driver transistor is coupled in series with the LED between a power supply node and a ground node;
   a first switch coupled between the LED and the source-drain path of the driver transistor;
   an amplifier, having non-inverting and inverting inputs, and having an output coupled to the gate of the driver transistor;
   a capacitor having: a first plate connected to a sample node; and a second plate connected to the non-inverting input of the amplifier;
   a second switch connected between the source of the driver transistor and the inverting input of the amplifier;
   a third switch connected between a reference voltage input and the sample node;
   a fourth switch connected between the reference voltage input and the non-inverting input of the amplifier;
   a fifth switch connected between the output of the amplifier and the sample node;
   a sixth switch connected between the output of the amplifier and the inverting input of the amplifier; and
   timing control circuitry to generate first and second clock phases to: close the fourth, fifth and sixth switches during the first clock phase; and close the first, second and third switches during the second clock phase.

2. The driver circuit of claim 1, further comprising:
   a variable resistor connected between the source of the driver transistor and the ground node; and
   a digital-to-analog converter (DAC) coupled to control the resistance of the variable resistor.

3. The driver circuit of claim 2, wherein the driver transistor has a body node coupled to the ground node, establishing a gate-to-body-node capacitance between the output of the amplifier and the ground node.

4. The driver circuit of claim 1, wherein the capacitor is a first capacitor, and the driver circuit further comprises:
   a second capacitor coupled between the reference voltage input and the ground node.

5. A photoplethysmography system, comprising:
   a transmitter channel, comprising: a light-emitting diode (LED); and an LED driver to control a bias and conduction of the LED so as to control an emission of light from the LED; and
   a receiver channel, comprising: a photodiode; an amplifier having an input coupled to the photodiode to generate a received light signal corresponding to current conducted by the photodiode in response to light impinging the photodiode; and a noise/ripple remover circuit having a first input coupled to an output of the amplifier, and a second input coupled to receive a signal from the transmitter channel corresponding to current conducted by the LED, for removing a transmitter noise component from the received light signal responsive to the signal from the transmitter channel;
   the LED driver comprising:
   a driver transistor having a source, a drain and a gate, wherein a source-drain path of the driver transistor is coupled in series with the LED between a power supply node and a ground node;
   a first switch coupled between the LED and the source-drain path of the driver transistor;
   an amplifier, having non-inverting and inverting inputs, and having an output coupled to the gate of the driver transistor;
   a capacitor having: a first plate connected to a sample node; and a second plate connected to the non-inverting input of the amplifier;
   a second switch connected between the source of the driver transistor and the inverting input of the amplifier;
   a third switch connected between a reference voltage input and the sample node;
   a fourth switch connected between the reference voltage input and the non-inverting input of the amplifier;
   a fifth switch connected between the output of the amplifier and the sample node;

a sixth switch connected between the output of the amplifier and the inverting input of the amplifier; and timing control circuitry to generate first and second clock phases to: close the fourth, fifth and sixth switches during the first clock phase; and close the first, second and third switches during the second clock phase.

6. The system of claim 5, wherein the signal from the transmitter channel comprises a voltage in a series path between a cathode of the LED and the source-drain path of the driver transistor; and wherein the noise/ripple remover circuit is configured to determine the current conducted by the LED responsive to the voltage signal from the transmitter channel and an AC resistance of the LED.

7. The system of claim 5, wherein the transmitter channel comprises a current sensor to sense current conducted in the series path of the LED and the source-drain path of the driver transistor; and wherein the signal from the transmitter comprises a signal from the current sensor.

8. The system of claim 5, wherein the LED driver and the noise/ripple remover circuit are formed in a same integrated circuit as one another.

9. The system of claim 5, wherein the LED driver further comprises:
 a variable resistor connected between the source of the driver transistor and the ground node; and
 a digital-to-analog converter (DAC) coupled to control the resistance of the variable resistor.

10. The system of claim 9, wherein the driver transistor has a body node coupled to the ground node, establishing a gate-to-body-node capacitance between the output of the amplifier and the ground node.

11. The system of claim 5, wherein the capacitor is a first capacitor, and the driver circuit further comprises:
 a second capacitor coupled between the reference voltage input and the ground node.

12. The system of claim 5, wherein the noise/ripple remover circuit comprises digital logic.

* * * * *